(12) United States Patent
Kudo (10) Patent No.: US 11,768,258 B2
(45) Date of Patent: Sep. 26, 2023

(54) SIGNAL SEPARATING APPARATUS, SIGNAL SEPARATING METHOD, AND NON-TRANSITORY RECORDING MEDIUM

(71) Applicant: Shunsuke Kudo, Kanagawa (JP)

(72) Inventor: Shunsuke Kudo, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 181 days.

(21) Appl. No.: 16/952,094

(22) Filed: Nov. 19, 2020

(65) Prior Publication Data

US 2021/0156930 A1   May 27, 2021

(30) Foreign Application Priority Data

Nov. 27, 2019 (JP) ................................ 2019-214679
Jul. 30, 2020 (JP) ................................ 2020-129329

(51) Int. Cl.
| | |
|---|---|
| *A61B 5/245* | (2021.01) |
| *A61B 5/369* | (2021.01) |
| *G16H 50/70* | (2018.01) |
| *G01R 33/00* | (2006.01) |
| *G16H 40/67* | (2018.01) |

(52) U.S. Cl.
CPC ......... *G01R 33/0029* (2013.01); *A61B 5/245* (2021.01); *A61B 5/369* (2021.01); *G16H 40/67* (2018.01); *G16H 50/70* (2018.01)

(58) Field of Classification Search
CPC .................................................. G01R 33/0029
See application file for complete search history.

(56) References Cited

U.S. PATENT DOCUMENTS

| | | | |
|---|---|---|---|
| 2013/0109954 A1* | 5/2013 | Simola .................. | A61B 5/245 600/409 |
| 2019/0000389 A1* | 1/2019 | Hikida ................. | G01R 33/035 |
| 2019/0125268 A1* | 5/2019 | Taulu .................... | A61B 5/369 |
| 2021/0186400 A1* | 6/2021 | Taulu ................... | A61B 5/4064 |

FOREIGN PATENT DOCUMENTS

| | | |
|---|---|---|
| JP | 2013-102947 | 5/2013 |
| JP | 2018-004286 | 1/2018 |
| JP | 2018-072947 | 5/2018 |
| JP | 2019-013284 | 1/2019 |
| WO | WO2006/114473 A1 | 11/2006 |
| WO | WO2013/111072 A1 | 8/2013 |

OTHER PUBLICATIONS

Kensuke Sekihara, et al., "Dual signal subspace projection (DSSP): a novel algorithm for removing large interference in biomagnetic measurements" Journal of Neural Engineering 13 (2016) 036007, p. 1-19.

* cited by examiner

*Primary Examiner* — Mohamed Charioui
(74) *Attorney, Agent, or Firm* — XSENSUS LLP (57) ABSTRACT

A signal separating apparatus includes circuitry to separate a signal of interest and other signal other than the signal of interest from each other in accordance with spatial information on a plurality of sensors installed at locations different from each other. The circuitry sets a parameter based on a spread of a subspace of the signal of interest, determines a degree of separation that serves as an index indicative of whether the set parameter is appropriate, and separates the signal of interest and the other signal from each other using the degree of separation.

14 Claims, 9 Drawing Sheets

SIGNAL SEPARATING APPARATUS, SIGNAL SEPARATING METHOD, AND NON-TRANSITORY RECORDING MEDIUM

CROSS-REFERENCE TO RELATED APPLICATIONS

This patent application is based on and claims priority pursuant to 35 U.S.C. § 119(a) to Japanese Patent Application No. 2019-214679, filed on Nov. 27, 2019, and Japanese Patent Application No. 2020-129329, filed on Jul. 30, 2020, in the Japan Patent Office, the entire disclosure of which is hereby incorporated by reference herein.

BACKGROUND

Technical Field

The present disclosure relates to a signal separating apparatus, a signal separating method, and a non-transitory recording medium.

Description of the Related Art

In the related art, disturbing signals and artifacts that are noise measured along with a signal of interest by a biomagnetism measuring apparatus such as a magnetoencephalography (MEG) measuring device hinder analysis of the signal of interest. Thus, the disturbing signals and artifacts are desirably removed.

There are techniques of separating signals to signal subspaces and removing undesirable signals in order to remove disturbing signals and artifacts measured in multichannel magnetic field measurements, multichannel electrical charge potential measurements, or the like. For example, there is disclosed a technique of spatially separating signals based on a physical model using the Maxwell's equations.

The techniques of removing disturbing signals and artifacts using spatial separation of the related art require setting of a parameter. However, there is no index indicative of whether the parameter is appropriate, and trials need to be performed using the final processing result. Therefore, an easy and appropriate spatial separation technique is desired.

SUMMARY

Example embodiments include a signal separating apparatus including circuitry to separate a signal of interest and other signal other than the signal of interest from each other in accordance with spatial information on a plurality of sensors installed at locations different from each other. The circuitry sets a parameter based on a spread of a subspace of the signal of interest, determines a degree of separation that serves as an index indicative of whether the set parameter is appropriate, and separates the signal of interest and the other signal from each other using the degree of separation.

Example embodiments include a signal separating apparatus including circuitry to create a projection matrix for separating a signal of interest and other signal other than the signal of interest from each other in accordance with spatial information on a plurality of sensors installed at locations different from each other. The circuitry sets a space suitable for a region in which the signal of interest is possibly generated.

BRIEF DESCRIPTION OF THE SEVERAL VIEWS OF THE DRAWINGS

A more complete appreciation of the disclosure and many of the attendant advantages and features thereof can be readily obtained and understood from the following detailed description with reference to the accompanying drawings, wherein.

The accompanying drawings are intended to depict embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Embodiments of a signal separating apparatus, a program, and a signal separating method will be described in detail below with reference to the accompanying drawings.

Figure 1:
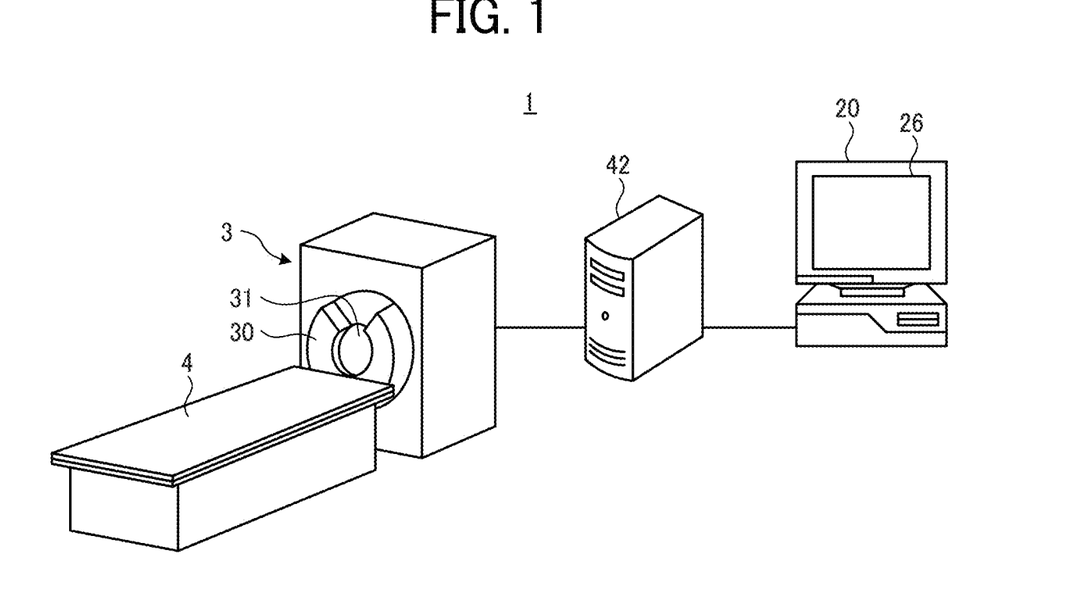
FIG. 1 is a diagram illustrating an example of a configuration of an information processing system according to a first embodiment.

FIG. 1 is a diagram illustrating an example of a configuration of an information processing system 1 according to a first embodiment. Referring to FIG. 1, the information processing system 1 measures a plurality of kinds of biosignals, for example, MEG signals and electroencephalography (EEG) signals, and displays the measured signals. The information processing system 1 includes a measuring apparatus 3, a data recording server 42, and an information processing apparatus 20. The information processing apparatus 20 includes a display 26 that displays signal information (measurement information) obtained in measurements and analysis results. The data recording server 42 and the information processing apparatus 20 are illustrated as separate apparatuses in FIG. 1; however, at least part of the data recording server 42 may be incorporated into the information processing apparatus 20.

A subject lies on their back on a measurement table 4 with electrodes (or sensors) for EEG measurement attached to their head such that the head is placed at a hollow 31 of a dewar 30 of the measuring apparatus 3. The dewar 30 is a vessel that preserves a cryogenic environment using liquid helium. Many magnetic sensors for MEG measurement are disposed inside the hollow 31 of the dewar 30. The measuring apparatus 3 collects EEG signals from the electrodes and MEG signals from the magnetic sensors and outputs the collected biosignals (measurement information) to the data recording server 42. The measurement information recorded in the data recording server 42 is read to and is displayed and analyzed by the information processing apparatus 20. The dewar 30 including the magnetic sensors and the measurement table 4 are commonly disposed in a magnetically shielded room; however, illustration of the magnetically shielded room is omitted in FIG. 1 for convenience.

As described above, the measuring apparatus 3 is a biomagnetism measuring apparatus such as an MEG measuring device and functions as a multichannel measuring apparatus. In the measuring apparatus 3 which is a multi-channel measuring apparatus, locations and orientations of the many magnetic sensors for MEG measurement are known. Thus, when a signal source close to the group of magnetic sensors is assumed, the measuring apparatus 3 is capable of calculating response values of the magnetic sensors.

The information processing apparatus 20 displays waveforms of the MEG signals from the plurality of magnetic sensors and waveforms of the EEG signals from the plurality of electrodes in synchronization with each other on the same time axis. EEG signals each represent, as a voltage value across the electrodes, electrical activities of nerve cells (a flow of ionic electrical charge that occurs at dendrites of neurons at the time of synaptic neurotransmission). MEG signals each represent a small fluctuation in the magnetic field caused by electrical activities of the brain. The magnetic field of the brain is detected by highly sensitive superconducting quantum unit interference device (SQUID) sensors.

Figure 2:
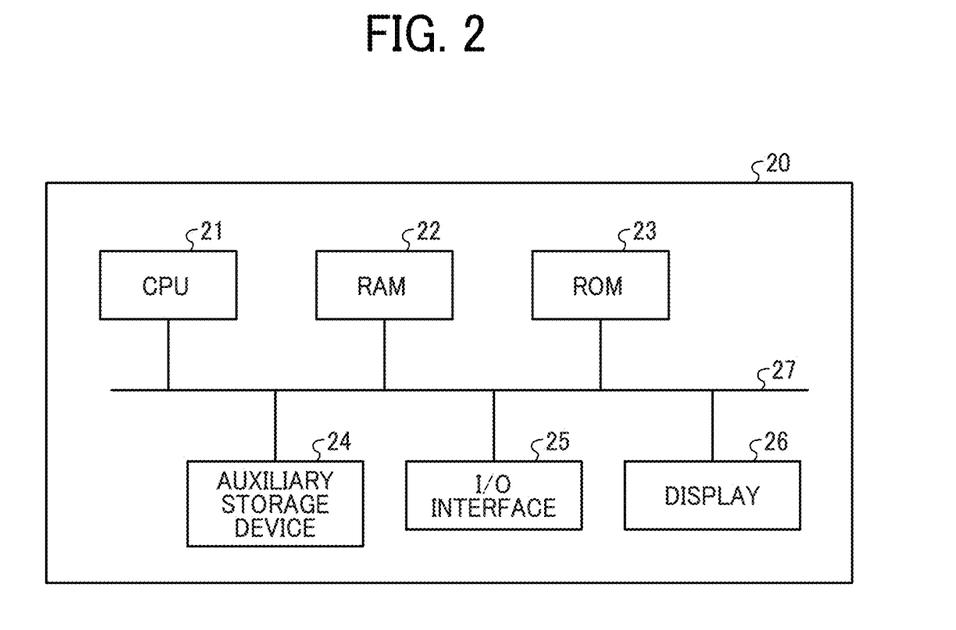
FIG. 2 is a block diagram illustrating an example of a hardware configuration of an information processing apparatus.

FIG. 2 is a block diagram illustrating an example of a hardware configuration of the information processing apparatus 20. The information processing apparatus 20 includes a central processing unit (CPU) 21, a random access memory (RAM) 22, a read-only memory (ROM) 23, an auxiliary storage device 24, an input/output (I/O) interface 25, and the display 26. The CPU 21, the RAM 22, the ROM 23, the auxiliary storage device 24, the IO interface 25, and the display 26 are coupled to each other by a bus 27.

The CPU 21 controls operations of the entire information processing apparatus 20 and performs various kinds of information processing. The CPU 21 also executes an information processing program stored in the ROM 23 or the auxiliary storage device 24 to control operations of displaying screens such as a measurement recording screen and an analysis screen.

The information processing program executed by the information processing apparatus 20 in this embodiment is recorded as a file of an installable format or an executable format on a non-transitory computer-readable recording medium such as a compact disc read-only memory (CR-ROM), a flexible disk (FD), a compact disc recordable (CD-R), or a digital versatile disc (DVD).

Alternatively, the information processing program executed by the information processing apparatus 20 in this embodiment may be stored on a computer connected to a network such as the Internet and may be downloaded and provided to the information processing apparatus 20 via the network. Alternatively, the information processing program executed by the information processing apparatus 20 in this embodiment may be provided or distributed to the information processing apparatus 20 via a network such as the Internet.

Alternatively, the information processing program executed by the information processing apparatus 20 in this embodiment may be preinstalled in the ROM or the like so as to be provided to the information processing apparatus 20.

The RAM 22 is used as a workspace for the CPU 21. Examples of the RAM 22 may include a nonvolatile RAM that stores major control parameters and information. The ROM 23 stores a program such as a basic input/output program. The information processing program according to this embodiment of the present disclosure may be stored in the ROM 23.

The auxiliary storage device 24 is a storage device such as a solid state drive (SSD), a hard disk drive (HDD), or the like. The auxiliary storage device 24 stores, for example, the information processing program for controlling operations of the information processing apparatus 20, various kinds of data and files used in the operations of the information processing apparatus 20, and so on.

The I/O interface 25 includes both a user interface such as a touch panel, a keyboard, display screens, operations buttons, and so on and a communication interface that acquires information from various sensors or the data recording server 42 and outputs analysis information to another electronic device.

The measurement recording screen and the analysis screen are displayed on the display 26, and the screens are updated in response to an input/output operation performed via the I/O interface 25.

Figure 3:
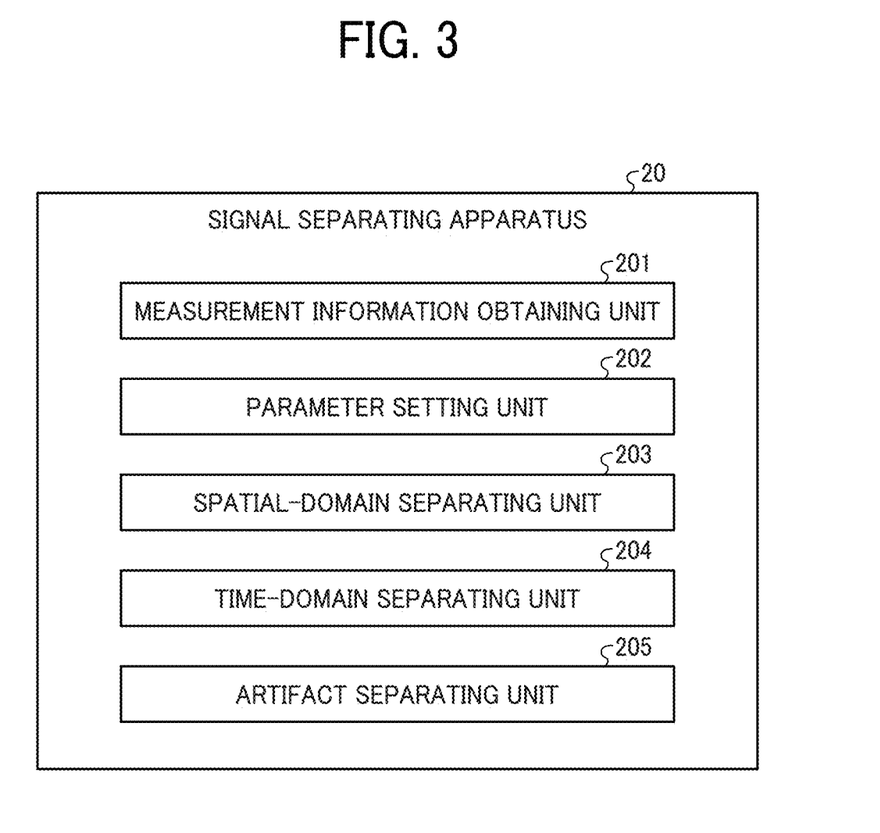
FIG. 3 is a block diagram illustrating an artifact removing function of the information processing apparatus.

Description is now given of a function of removing disturbing signals and artifacts which are noise measured along with a signal of interest by the measuring apparatus 3 among functions of the information processing apparatus 20 according to this embodiment. FIG. 3 is a block diagram illustrating an artifact removing function of the information processing apparatus 20.

The information processing apparatus 20 functions as a signal separating apparatus, and includes a measurement information obtaining unit 201, a parameter setting unit 202, a spatial-domain separating unit 203, a time-domain separating unit 204, and an artifact separating unit 205.

The CPU 21 reads out and executes the information processing program stored in the ROM 23 or the auxiliary storage device 24 to implement the measurement information obtaining unit 201, the parameter setting unit 202, the spatial-domain separating unit 203, the time-domain separating unit 204, and the artifact separating unit 205.

The measurement information obtaining unit 201 obtains biosignals (measurement information) measured by the measuring apparatus 3 from the data recording server 42. The measurement information obtaining unit 201 stores biosignals (measurement information), which serve as sensor information, measured by the measuring apparatus 3 in the auxiliary storage device 24.

The parameter setting unit 202 uses spatial information on the locations and orientations of the magnetic sensors of the measuring apparatus 3 to select and set an appropriate parameter for spatial separation (described below).

That is, the parameter setting unit 202 sets, as the parameter, a value calculated on the basis of a spread of a subspace of the signal of interest.

The parameter setting unit 202 may select, from among parameter option, a parameter based on a predetermined criterion relating to the spread of the subspace of the signal of interest and set the selected parameter as the parameter.

Alternatively, the parameter setting unit 202 may replace the value calculated on the basis of the spread of the subspace of the signal of interest with a previously set value and set the previously set value as the parameter.

The spatial-domain separating unit 203 uses a projection matrix created on the basis of the parameter set by the parameter setting unit 202 to separate an inside and an outside of the subspace of the signal of interest from each other.

The time-domain separating unit 204 determines a time-direction basis vector of each subspace separated by the spatial-domain separating unit 203 through singular value decomposition or the like to separate a component other than the signal of interest from the signal of interest.

The artifact separating unit 205 functions as a signal separating unit and removes disturbing signals and artifact components on the basis of the time-direction basis vectors. The artifact separating unit 205 also determines a degree of (spatial) separation (a separation gain serving as the degree of separation in this embodiment), as an index indicative of whether the parameter set by the parameter setting unit 202 is appropriate.

An example of determining the parameter by the measuring apparatus 3 will now be described.

Figure 4:
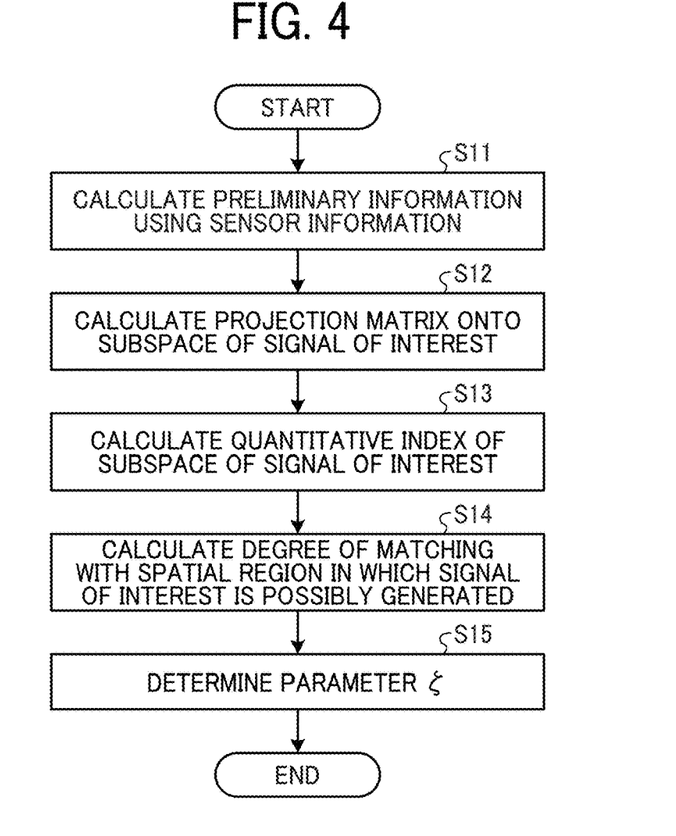
FIG. 4 is a flowchart illustrating a flow of a parameter determining process.

FIG. 4 is a flowchart illustrating a flow of a parameter determining process. Description is given here of a processing example based on the DSSP method (see K. Sekihara, Y. Kawabata, S. Ushio, S. Sumiya, S. Kawabata. Y. Adachi, S. S. Nagarajan, "Dual signal subspace projection (DSSP): a novel algorithm for removing large interference in biomagnetic measurements". Journal of Neural Engineering, vol. 13, no. 3, 036007, 2016), which is one of methods of removing disturbing signals and artifacts using spatial separation.

Figure 5:
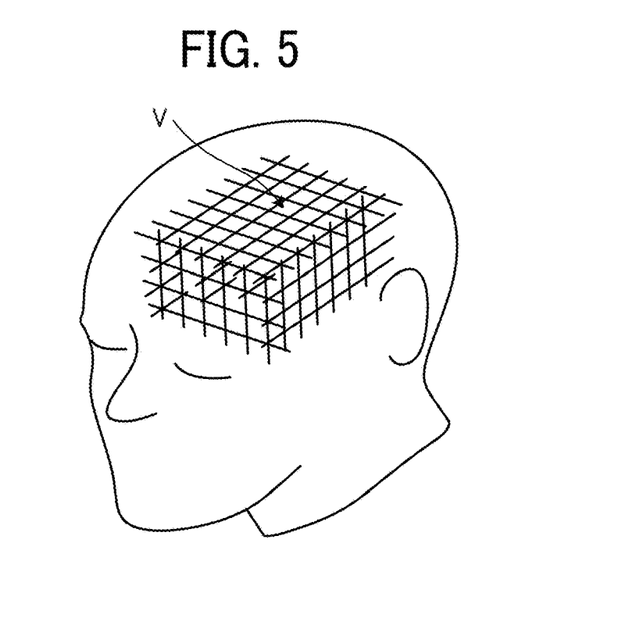
FIG. 5 is a diagram illustrating an example in which a region of interest is divided into voxels.

The spatial-domain separating unit 203 divides a region of interest (a region in which a signal of interest to be observed is possibly generated) set in advance into voxels V as illustrated in FIG. 5. As illustrated in FIG. 4, the spatial-domain separating unit 203 calculates, based on spatial information on the locations and orientations of M magnetic sensors of the dewar 30 of the measuring apparatus 3, sensor responses $L(r_i)$ in the case where the signal source exists in an $r_i$-th voxel V in the region of interest for all the voxels V in the region of interest and calculates preliminary information F as expressed by Expression (1) below (step S11).

$$F=[L(r_1), \ldots ,L(r_N)] \quad (1)$$

Then, the time-domain separating unit 204 sets, as the basis vector of the subspace of the signal of interest, an eigenvector of the Gram matrix of the preliminary information F calculated in step S11, and calculates a projection matrix P to the subspace of the signal of interest as expressed by Expressions (2) and (3) below (step S12). When the time-domain separating unit 204 calculates the projection matrix P to the subspace of the signal of interest, the projection matrix P is created by reducing the dimension of the preliminary information F. The dimension of the projection matrix P thus serves as the dimension $\zeta$ ($0<\zeta<M$) of the subspace of the signal of interest.

$$FF^T = [e_1, \ldots, e_M] \begin{bmatrix} \gamma_1 & 0 & \cdots & 0 \\ 0 & \gamma_2 & \cdots & 0 \\ \vdots & \vdots & \ddots & \vdots \\ 0 & 0 & \cdots & \gamma_M \end{bmatrix} \begin{bmatrix} e_1^T \\ \vdots \\ e_M^T \end{bmatrix} \quad (2)$$

$$P = [e_1, \ldots, e_\zeta][e_1, \ldots, e_\zeta]^T \quad (3)$$

Note that the processing described above is known as part of the DSSP method which is one of the methods of removing disturbing signals and artifacts using spatial separation.

Then, the artifact separating unit 205 calculates a quantitative index of the subspace of the signal of interest (step S13). The quantitative index is used for evaluating the projection performance of the projection matrix P, which projects responses (hereinafter, also referred to as an original signal) B(x, y, z) of the plurality of magnetic sensors of the measuring apparatus 3 to a signal generated at any location onto the subspace of the signal of interest and separates the original signal into a signal 1 containing the signal of interest and a signal 2 not containing the signal of interest.

More specifically, the artifact separating unit 205 uses a ratio of strength of the signal resulting from separation to strength of the original signal B(x, y, z) to define the quantitative index of the subspace of the signal of interest as expressed by Expression (4) below. The signal 2 ((I−P)B) not containing the signal of interest is used in Expression (4); however, using the signal 1 (PB) containing the signal of interest has the same meaning. The point here is that to which of the signal 1 and the signal 2 and at what ratio the original signal is separated. Description will be given here of projection to an outer subspace. The artifact separating unit 205 determines gains $\phi(x, y, z)$ of the subspace with respect to the original signals B(x, y, z) corresponding to various locations.

$$\Phi(x, y, z) = \frac{|(I - P)B(x, y, z)|}{|B(x, y, z)|} \quad (4)$$

Then, the artifact separating unit 205 calculates the degree of matching between a region (whitish region) $R_\phi$ in which the gain $\phi$ is less than or equal to a threshold value and the region of interest $R_I$ set in step S11 (step S14). This embodiment assumes the additional use of another index, and a score $\lambda$ of the Jaccard index which is one of indices for the degree of matching is determined as expressed by Expression (5) below.

$$\lambda(\zeta) = \frac{R_\phi \cap R_I}{R_\phi \cup R_I} \quad (5)$$

As other methods of determining the degree of matching, methods of determining a commonly used degree of matching such as the dice index or the volume similarly, the binary classification model evaluation index such as accuracy or the F score, and probability-based similarity are usable.

In the case where binarization is not performed, the degree of matching can be determined using various probability distributions and evaluation indices therefor such as the receiver operating characteristic (ROC) curve and the area under the curve therefor or using the image comparing method. Note that the aforementioned threshold value is optimizable using the probability distribution.

Subsequently, the artifact separating unit 205 determines ζ that gives the maximum score λ as expressed by Expression (6) below to determine ζ with which the subspace of the signal of interest that is most suitable for the region of interest is created (step S15). argmaxλ(ζ)

$$0 < \zeta < M \tag{2}$$

The process described above is a method having a parameter that influences the spread of the subspace of the signal of interest similarly to the DSSP method and is effective.

Description will be given next of a specific example of the spread of the subspace of a signal of interest and the index for the subspace of the signal of interest (based on the DSSP method).

Figure 6A:
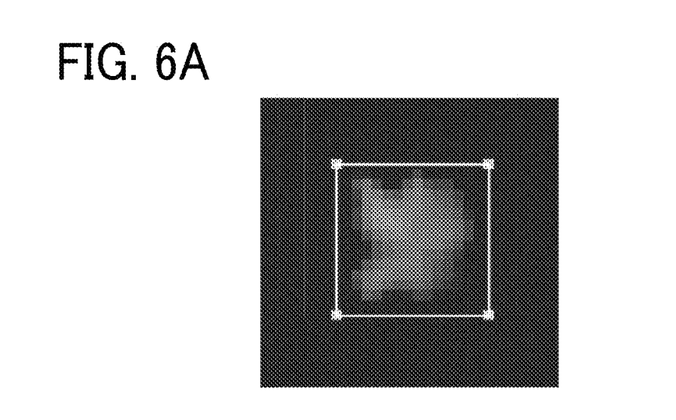
FIGS. 6A to 6G are diagrams describing a spread of a subspace of a signal of interest and graphs describing an index for the subspace of the signal of interest (based on the dual signal subspace projection (DSSP) method)
Figure 6B:
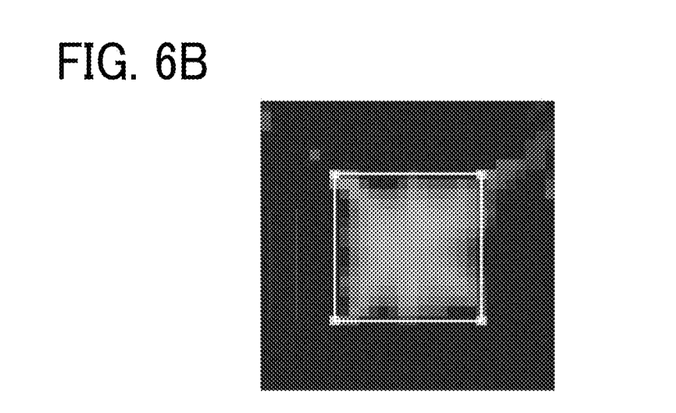
Figure 6C:
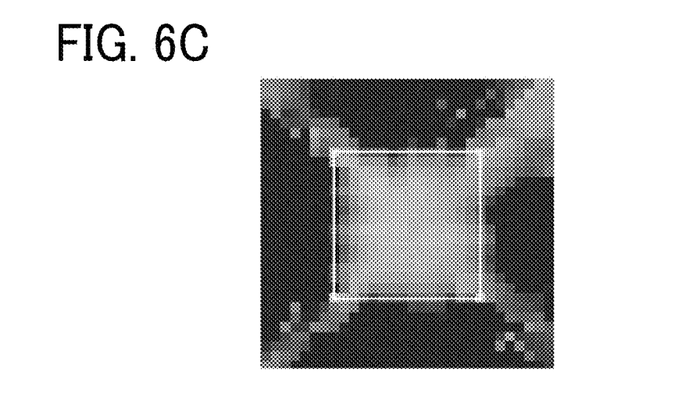

FIGS. 6A to 6G are diagrams describing a spread of a subspace of a signal of interest and graphs describing an index for the subspace of the signal of interest (based on the DSSP method). FIGS. 6A to 6C are diagrams depicting the values of the gain ϕ for different values of the dimension ζ of the subspace of the signal of interest.

As illustrated in FIGS. 6A to 6C, the spatial-domain separating unit 203 divides a region of interest (a region in which a signal to be left is generated) into voxels V to set rectangular solids. Then, the spatial-domain separating unit 203 displays a predetermined axial sectional view of the set rectangular solids. That is, white frames illustrated in FIGS. 6A to 6C represent ranges of the set region of interest. Referring to FIGS. 6A to 6C, the more whitish the color, the smaller the gain of the signal generated at that location being separated into the signal 2 not containing the signal of interest. This indicates that most of the signal generated at that location is separated into the signal 1 containing the signal of interest. Therefore, because of the assumption that the signal in the region of interest is the signal of interest, it is ideal that the region in the white frame becomes more whitish, and the whitish color is suppressed and the color becomes blackish in the region outside the white frame. Thus, the whitish region represents the spread of the subspace of the signal of interest.

FIG. 6A indicates that the subspace of the signal of interest is smaller than the defined region of interest and thus is insufficient. In contrast, in FIG. 6C, the subspace of the signal of interest is larger than the defined region of interest. This indicates that the signal of interest is contaminated with disturbing signals from outside the region of interest. This suggests that the subspace of the signal of interest in FIG. 6B is optimum. However, determining the degree of matching between the region of interest and the region of the subspace of the signal of interest to quantify the spread of the subspace of the signal of interest also allows for selection of the optimum parameter.

Figure 6D:
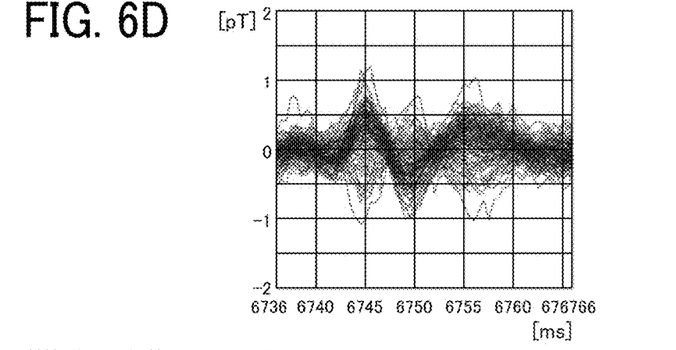
Figure 6E:
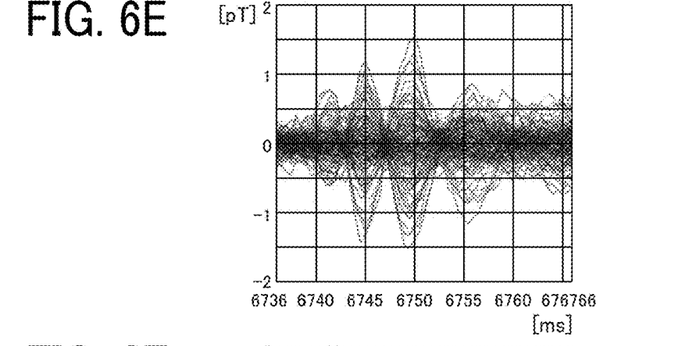
Figure 6F:
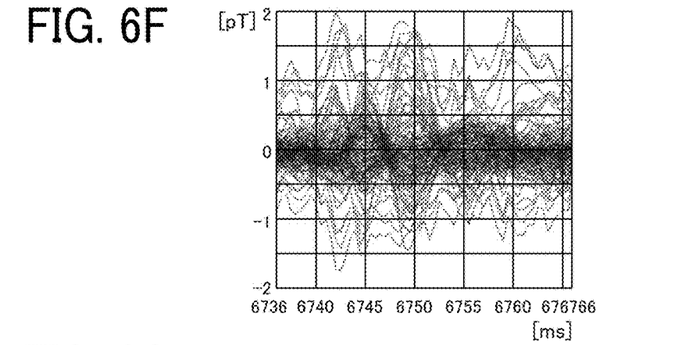
Figure 6G:
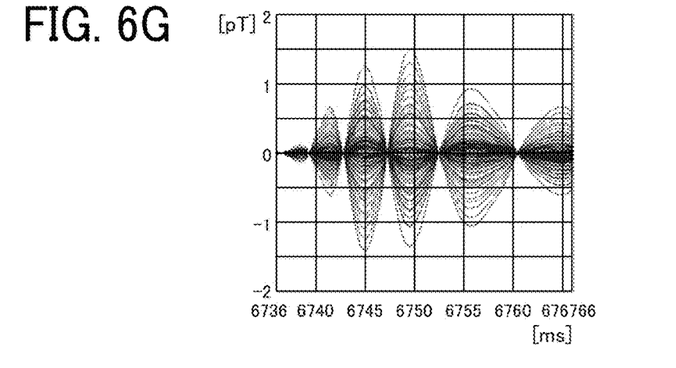

Graphs illustrated in FIGS. 6D, 6E, and 6F depict waveforms resulting from removal of a disturbing signal using the above-described subspaces of the signal of interest illustrated in FIGS. 6A, 6B, and 6C, respectively. The disturbing signal used at that time is a disturbing signal recorded with the measuring apparatus 3 which is a MEG measuring device in a state in which a noise source is actually placed near the left collarbone. FIGS. 6D, 6E, and 6F illustrate data resulting from superimposition of a pseudo-biosignal illustrated in FIG. 6G and this disturbing signal. It is apparent that the waveform illustrated in FIG. 6E is the closest to the correct waveform illustrated in FIG. 6G.

This indicates that when the spread of the subspace of the signal of interest is set to match the region of interest, a good final result is obtained. Thus, the artifact separating unit 205 uses the spread of the subspace of the signal of interest as an index to determine the parameter.

As described above, in accordance with this embodiment, determining the gain of separation as an index indicative of whether the set parameter is appropriate allows for creation of an appropriate subspace of the signal of interest.

Thus, in accordance with this embodiment, the parameter no longer needs to be searched for by trial and error. In addition, in accordance with this embodiment, alteration of the result due to selection of the different parameters by different analysists becomes unlikely. Further, in accordance with this embodiment, the subspace of the signal of interest is successfully created for each patient by the MEG measuring device.

A second embodiment will be described next.

The tSSS method is used in the second embodiment. This is different from the first embodiment in which the DSSP method is used. Description of the same configurations as those of the first embodiment is omitted in the following description of the second embodiment, and differences from the first embodiment will be described.

FIGS. 7A to 7G are diagrams describing a spread of a subspace of a signal of interest and graphs describing an index for the subspace of the signal of interest (based on the tSSS method) in accordance with the second embodiment.

Figure 7A:
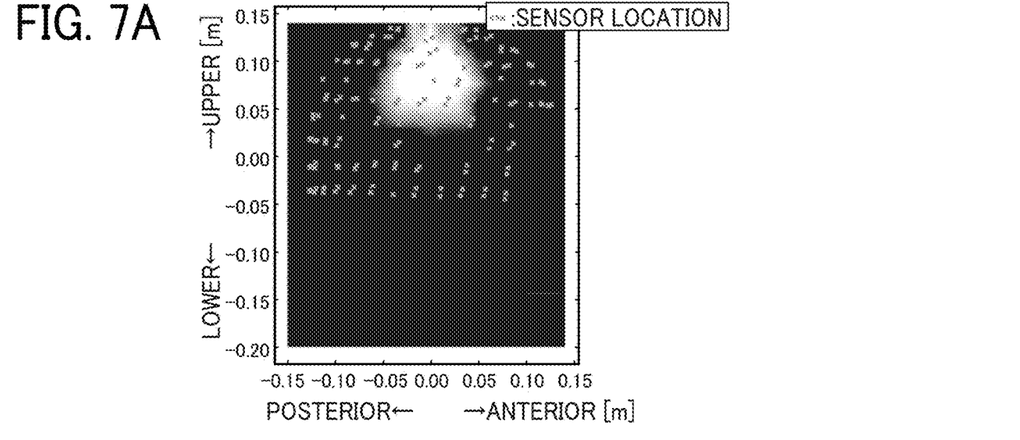
FIGS. 7A to 7G are diagrams describing a spread of a subspace of a signal of interest and graphs describing an index for the subspace of the signal of interest (based on the temporally extended signal space separation (tSSS) method) in accordance with a second embodiment.
Figure 7B:
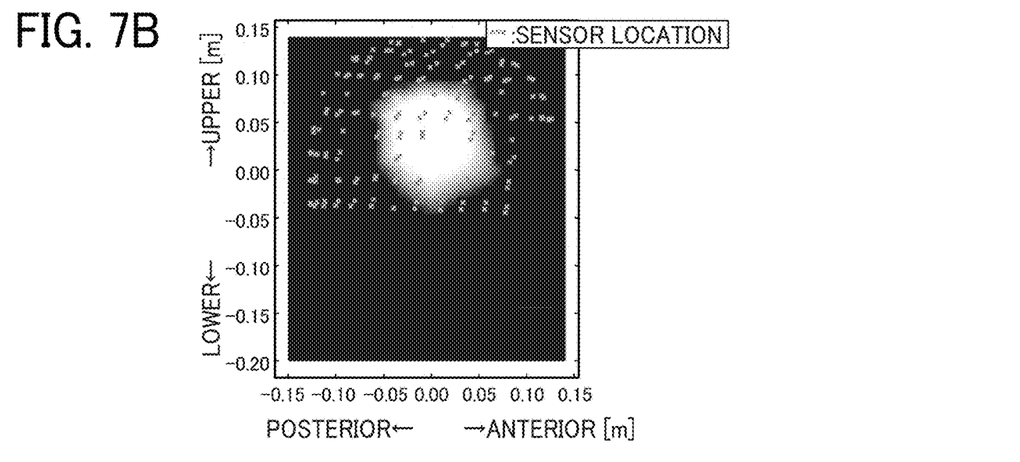
Figure 7C:
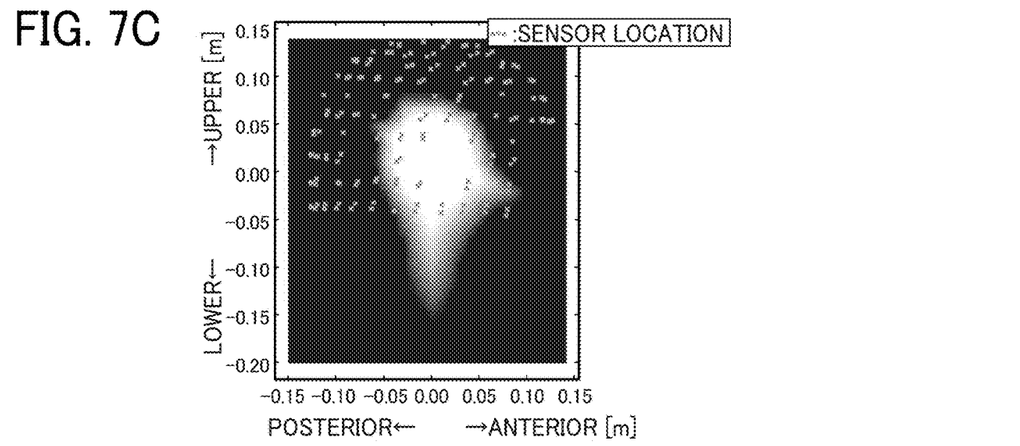

In the tSSS method, a set spherical center is a parameter relating to the spread of the subspace of the signal of interest. FIGS. 7A, 7B, and 7C are diagrams depicting the values of the gain ϕ for the different spherical centers.

The way in which the subspace of the signal of interest spreads is different from the DSSP method illustrated in FIGS. 6A to 6C. Thus, FIGS. 7A to 7C are sagittal central sectional views, and the right side and left side in FIGS. 7A to 7C represent the anterior side and the posterior side, respectively. In the tSSS method, the region of interest is represented by a sphere. Thus, locations of sensors assumed to be installed in this case are also projected in FIGS. 7A to 7C.

The region of interest illustrated in FIGS. 7A to 7C is a portion in the region where the sensors are installed. Referring to FIGS. 7A to 7C, the more whitish the color, the smaller the gain of the signal generated at that location being separated into the signal 2 not containing the signal of interest. This indicates that most of the signal generated at that location is separated into the signal 1 containing the signal of interest. Therefore, because of the assumption that the signal within the region of interest is the signal of interest, it is ideal that the region around the spherical center becomes more whitish, and the whitish color is suppressed and the color becomes blackish in the other region. Thus, the whitish region represents the spread of the subspace of the signal of interest.

In FIG. 7A, the subspace of the signal of interest is smaller than the defined region of interest and thus is insufficient. In contrast, in FIG. 7C, the subspace of the signal of interest is larger than the defined region of interest. This indicates that the signal of interest is contaminated with disturbing signals from outside the region of interest. This suggests that the subspace of the signal of interest in FIG. 7B is optimum. However, determining the degree of matching between the region of interest and the region of the subspace of the signal of interest to quantify the spread of the subspace of the signal of interest also allows for selection of the optimum parameter.

Figure 7D:
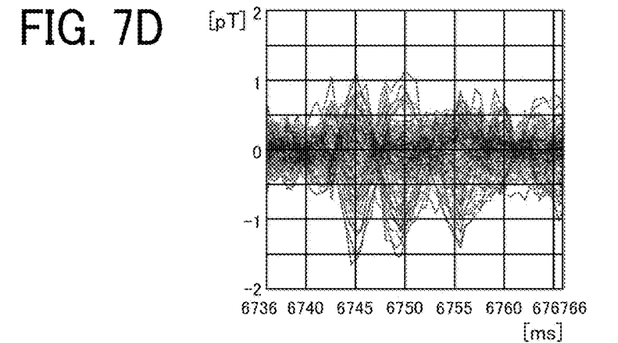
Figure 7E:
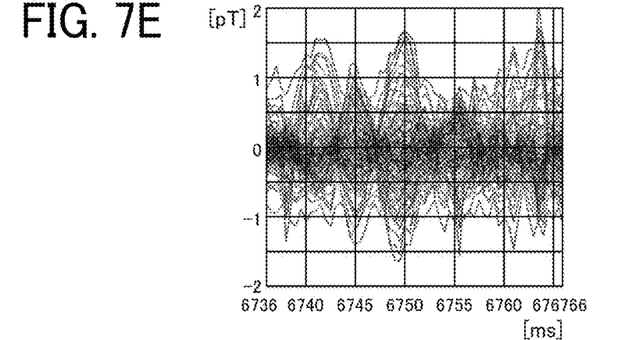
Figure 7F:
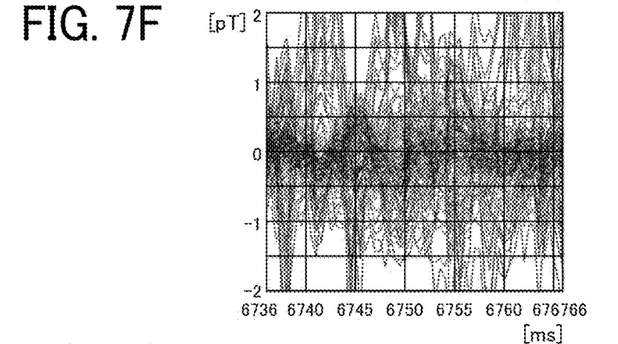
Figure 7G:
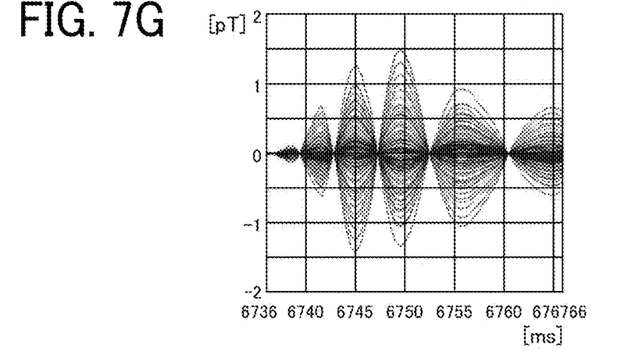

Graphs illustrated in FIGS. 7D, 7E, and 7F depict waveforms resulting from removal of a disturbing signal using the above-described subspaces of the signal of interest illustrated in FIGS. 7A, 7B, and 7C, respectively. The disturbing signal used at that time is a disturbing signal recorded with the measuring apparatus 3 which is a MEG measuring device in a state in which a noise source is actually placed near the left collarbone. FIGS. 7D, 7E, and 7F illustrate data resulting from superimposition of a pseudo-biosignal illustrated in FIG. 7G and this disturbing signal. It is apparent that the waveform illustrated in FIG. 7E is the closest to the correct waveform illustrated in FIG. 7G.

This indicates that when the spread of the subspace of the signal of interest is set to match the region of interest, a good final result is obtained. Thus, the artifact separating unit 205 uses the spread of the subspace of the signal of interest as an index to determine the parameter.

As described above, in accordance with this embodiment, also with the tSSS method, the spread of the subspace of the signal of interest is quantified on the basis of the ratio calculated for any signal source and an appropriate parameter is successfully determined on the basis of the quantified spread of the subspace of the signal of interest in the similar manner. This thus allows for creation of an appropriate subspace of the signal of interest.

A third embodiment will be described next.

The third embodiment describes a method of creating a subspace of a signal of interest in the measuring apparatus 3. Description of the same configurations as those of the first embodiment is omitted in the following description of the third embodiment, and differences from the first embodiment will be described.

Figure 8:
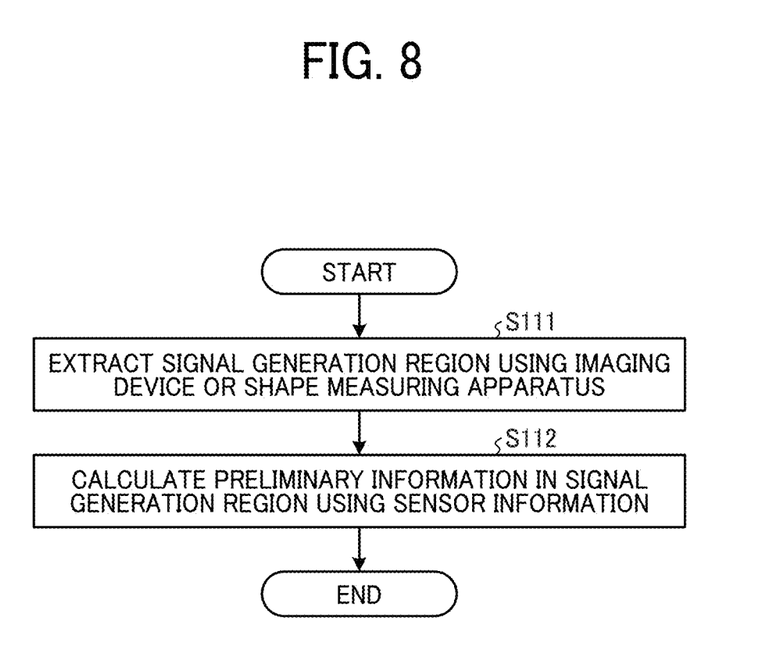
FIG. 8 is a flowchart illustrating a flow of creating a subspace of a signal of interest in accordance with a third embodiment.

FIG. 8 is a flowchart illustrating a flow of creating a subspace of a signal of interest in accordance with the third embodiment. The flowchart illustrated in FIG. 8 describes in detail the processing performed by the spatial-domain separating unit 203 in step S11 of FIG. 4 described in the first embodiment.

As illustrated in FIG. 8, the spatial-domain separating unit 203 uses information obtained from an information obtaining apparatus such as an imaging device or a shape measuring apparatus to manually or automatically extract a signal generation region (step S111).

For example, when the measuring apparatus 3 is a MEG measuring device, the spatial-domain separating unit 203 performs alignment based on the information obtained with an imaging device such as a magnetic resonance imaging (MRI) and locations of the magnetic sensors of the dewar 30 of the measuring apparatus 3 to create voxels or a mesh such that the region of interest substantially matches the actual signal generation region. The signal generation region is, for example, a region of the brain in the case of the MEG and indicates a region in which the signal of interest to be observed is possibly generated.

Then, the spatial-domain separating unit 203 uses sensor information measured with the measuring apparatus 3 and obtained via the measurement information obtaining unit 201 to calculate the preliminary information F in the signal generation region (step S12).

Figure 9A:
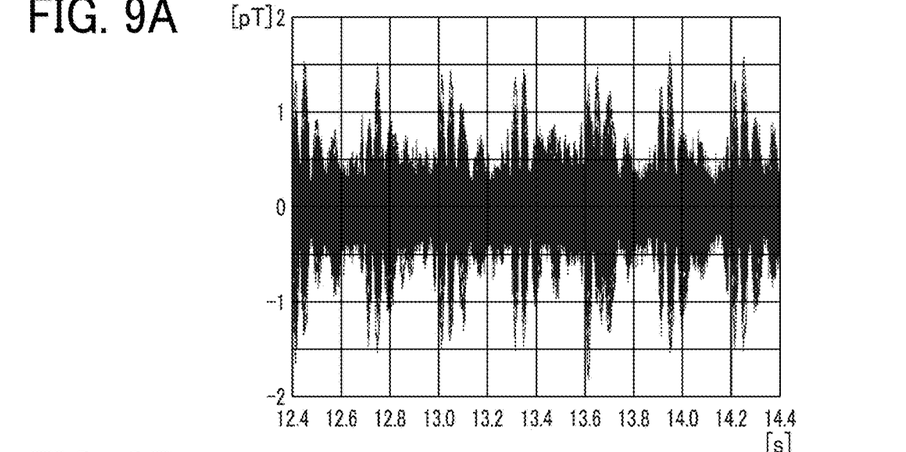
FIGS. 9A to 9C are graphs describing an index for a subspace of a signal of interest (based on the DSSP method).
Figure 9B:
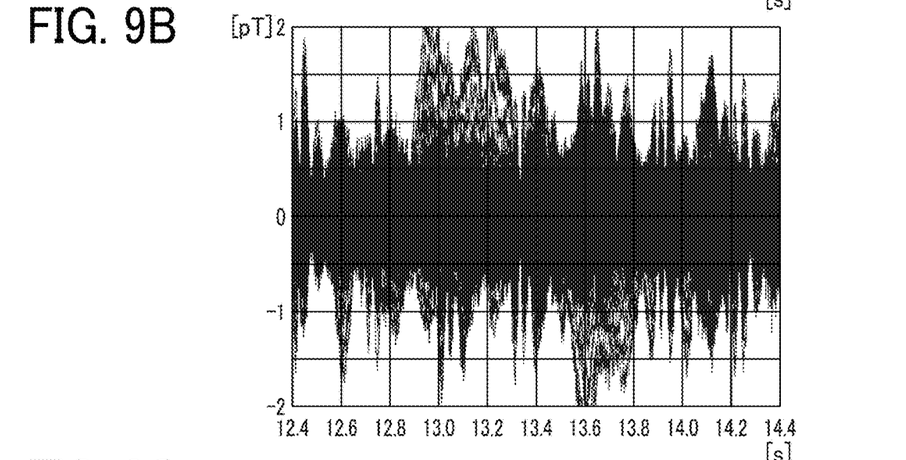
Figure 9C:
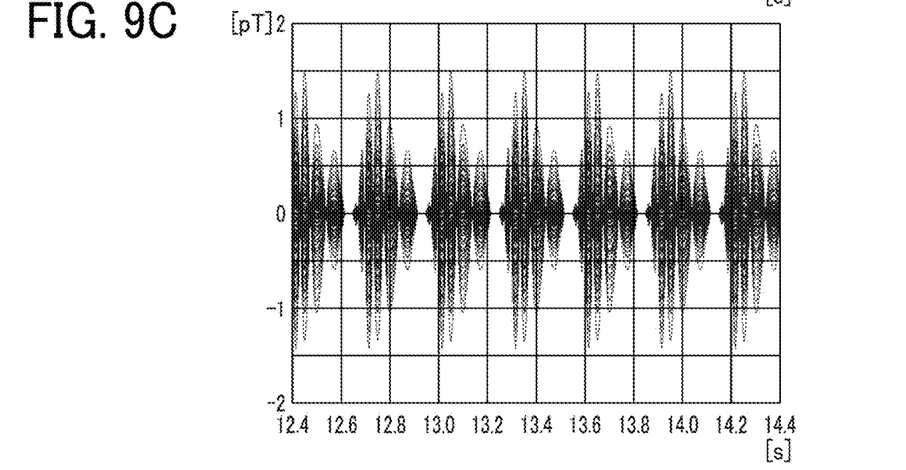

FIGS. 9A to 9C are graphs describing the index for the subspace of the signal of interest (based on the DSSP method). FIG. 9A illustrates a waveform resulting from DSSP using a projection matrix created with the voxels defined in step S111 of FIG. 8. FIG. 9B illustrates a waveform resulting from DSSP using a projection matrix created with the voxels defined by rectangular solids as described in FIGS. 6A to 6C. The disturbing signal used at that time is a disturbing signal recorded with the measuring apparatus 3 which is a MEG measuring device in a state in which a noise source is actually placed near the left collarbone. FIGS. 9A and 9B illustrate data resulting from superimposition of a pseudo-biosignal illustrated in FIG. 9C and this disturbing signal. It is apparent that the waveform illustrated in FIG. 9A is the closest to the waveform illustrated in FIG. 9C.

This indicates that the method of creating voxels by setting the region of interest to match the actual shape of the brain on the basis of information obtained through alignment based on the information obtained with an imaging device such as an MRI or a shape measuring apparatus and the locations of the magnetic sensors of the dewar 30 of the measuring apparatus 3 is useful when voxels are created.

Note that the method of representing the actual shape of the brain may be, but not limited to, any of a method of approximating the actual shape of the brain with a single sphere (single sphere model), a method of approximating the actual shape of the brain with a plurality of spheres (overlapping sphere model), a method of extracting the actual shape of the brain from imaging information, or the like.

As described above, in accordance with this embodiment, setting voxels suitable for the signal generation region (a region where a signal of interest to be observed is possibly generated) and creating a space result in improved spatial separation performance. Thus, the disturbing signal removal performance is successfully increased when an appropriate parameter is selected.

Although the example case where the living body is regarded to be the head has been described in detail in each of the embodiments, the living body is not limited to the head. For example, the living body may be the cervical vertebra subjected to the magnetospinography (MSG) or the like, and the living body tracking in MSG measurements is also within the scope of the present disclosure.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

In one example, the present invention may reside in: a signal separating apparatus comprising: circuitry configured to create a projection matrix for separating a signal of interest and other signal other than the signal of interest from each other in accordance with spatial information on a plurality of sensors installed at locations different from each other. The circuitry being configured to set a space suitable for a region in which the signal of interest is possibly generated.

For example, the circuitry is configured to set the space suitable for the region in which the signal of interest is possibly generated, using information obtained from an information obtaining apparatus.

In another example, a signal separating method includes: creating a projection matrix for separating a signal of interest and other signal other than the signal of interest from each other in accordance with spatial information on a plurality of sensors installed at locations different from each other, wherein the creating includes setting a space suitable for a region in which the signal of interest is possibly generated.

In another example, a non-transitory recording medium stores a plurality of instructions which, when executed by one or more processors, cause the processors to perform a signal separating method comprising: creating a projection matrix for separating a signal of interest and other signal other than the signal of interest from each other in accordance with spatial information on a plurality of sensors installed at locations different from each other, wherein the creating includes setting a space suitable for a region in which the signal of interest is possibly generated.

The invention claimed is:

1. A signal separating apparatus, comprising:
   circuitry configured to separate a signal of interest and another signal, different than the signal of interest, in accordance with spatial information on a plurality of sensors installed at locations different from each other, wherein
   to separate the signal of interest and the other signal, the circuitry is further configured to
      calculate a degree of matching between a first area and a second area, the first area being a region of subspace of the signal of interest and the second area being where the signal of interest is generated;
      set a spatial separation parameter based on the degree of matching;
      determine a degree of separation that serves as an index indicative of whether the set spatial separation parameter is appropriate; and
      separate the signal of interest and the other signal from each other using the degree of separation.

2. The signal separating apparatus according to claim 1, wherein the circuitry is configured to set, as the spatial separation parameter, a value calculated based on a spread of the subspace of the signal of interest.

3. The signal separating apparatus according to claim 1, wherein the circuitry is further configured to select, from among spatial separation parameter options, a first spatial separation parameter based on a predetermined criterion relating to a spread of the subspace of the signal of interest and set the selected first spatial separation parameter as the spatial separation parameter.

4. The signal separating apparatus according to claim 1, wherein the circuitry is further configured to replace a value calculated based on a spread of the subspace of the signal of interest with a previously set value and set the previously set value as the spatial separation parameter.

5. The signal separating apparatus according to claim 1, wherein the circuitry is further configured to quantify a spread of the subspace of the signal of interest.

6. The signal separating apparatus according to claim 1, wherein the circuitry is configured to
   set a first region in which the signal of interest is possibly generated, and
   separate an inside and an outside of the subspace of the signal of interest from each other using a projection matrix created based on the spatial separation parameter.

7. The signal separating apparatus according to claim 6, wherein the circuitry is further configured to determine a time-direction basis vector of each separated subspace and separate, from the signal of interest, a component other than the signal of interest.

8. The signal separating apparatus according to claim 6, wherein the circuitry is further configured to
   calculate the degree of matching between the subspace of the signal of interest and the first region in which the signal of interest is generated, and
   determine the spatial separation parameter using the degree of matching and using, as the index, a spread of the subspace of the signal of interest.

9. The signal separating apparatus according to claim 8, wherein the circuitry is configured to calculate the index relating to the spread of the subspace of the signal of interest, using a signal separation ratio between the signal of interest and the other signal.

10. The signal separating apparatus according to claim 1, wherein the circuitry is further configured to
    set the spatial separation parameter based on the degree of the degree of matching and a spread of the subspace of the signal of interest.

11. The signal separating apparatus according to claim 10, wherein the spread of the subspace of the signal of interest indicates variations of the signal of interest.

12. The signal separating apparatus according to claim 1, wherein the first area, which is the region of subspace of the signal of interest, is defined by a ratio of strength between the signal of interest before separation from the other signal and the signal of interest after space separation.

13. A signal separating method, comprising:
    separating a signal of interest and another signal, different than the signal of interest, in accordance with spatial information on a plurality of sensors installed at locations different from each other, the separating including:
       calculating a degree of matching between a first area and a second area, the first area being a region of subspace of the signal of interest and the second area being where the signal of interest is generated;
       setting a spatial separation parameter based on the degree of matching;
       determining a degree of separation that serves as an index indicative of whether the spatial separation parameter set in the setting is appropriate; and
       separating the signal of interest and the other signal from each other using the degree of separation.

14. A non-transitory recording medium storing a plurality of instructions which, when executed by one or more processors, cause processors to perform a signal separating method comprising:
    separating a signal of interest and another signal, different than the signal of interest, in accordance with spatial information on a plurality of sensors installed at locations different from each other, the separating including:
       calculating a degree of matching between a first area and a second area, the first area being a region of subspace of the signal of interest and the second area being where the signal of interest is generated;
       setting a spatial separation parameter based on the degree of matching;

determining a degree of separation that serves as an index indicative of whether the spatial separation parameter set in the setting is appropriate; and separating the signal of interest and the other signal from each other using the degree of separation.

* * * * *